US006653077B1

(12) United States Patent
Brenner

(10) Patent No.: US 6,653,077 B1
(45) Date of Patent: Nov. 25, 2003

(54) METHOD OF SCREENING FOR GENETIC POLYMORPHISM

(75) Inventor: Sydney Brenner, Cambridge (GB)

(73) Assignee: Lynx Therapeutics, Inc., Hayward, CA (US)

( * ) Notice: Subject to any disclaimer, the term of this patent is extended or adjusted under 35 U.S.C. 154(b) by 0 days.

(21) Appl. No.: 09/786,254

(22) PCT Filed: Aug. 31, 1999

(86) PCT No.: PCT/US99/20047

§ 371 (c)(1),
(2), (4) Date: Jul. 25, 2001

(87) PCT Pub. No.: WO00/14282

PCT Pub. Date: Mar. 16, 2000

Related U.S. Application Data

(60) Provisional application No. 60/099,147, filed on Sep. 4, 1998.

(51) Int. Cl.[7] ............................. C12Q 1/68; C12P 19/34
(52) U.S. Cl. ........................ 435/6; 435/91.1; 435/91.2; 435/91.5
(58) Field of Search ...................... 435/6, 91.2, 7.1, 435/91.5, 91.1

(56) References Cited

U.S. PATENT DOCUMENTS 5,595,895 A 1/1997 Miki et al. ............... 435/172.3
6,080,544 A * 6/2000 Weghorst et al. ............. 435/6
6,297,010 B1 * 10/2001 Stefano ..................... 435/6

OTHER PUBLICATIONS

Brown, Patrick O., "Genome Scanning Methods", *Current Opinion in Genetics and Development* 4:366–373 (1994).
Schumaker, J. M. et al., "Mutation Detection by Solid Phase Primer Extension" *Human Mutation* 7:346–354 (1996).
Nikiforov, T. T. et al., "Genetic Bit Analysis: a solid phase method for typing single nucleotide polymorphisms", *Nucleic Acids Research*, vol. 22, No. 20: 4167–4175 (1994).

Pastinen, T. et al., "Minisequencing: A Specific Tool for DNA Analysis and Diagnostics on Oligonucleotide Arrays", *Genome Research* 7:606–614 (1997).

International Search Report for Application No. PCT/US99/20047.

* cited by examiner

*Primary Examiner*—Carla J. Myers
(74) *Attorney, Agent, or Firm*—Peter J. Dehlinger; Lee Ann Gorthey; Perkins Coie LLP

(57) ABSTRACT

Method and materials are provided for screening for genetic polymorphism in a test population of DNA fragments. Heteroduplexes are formed between members of a test DNA population and their corresponding complements from a reference DNA population. Perfectly matched heteroduplexes are destroyed or separated from those containing mismatched sequences. Preferably, perfectly matched heteroduplexes are digested by a single stranded exonuclease which requires double stranded DNA as a substrate, such as *E. coli* exonuclease III. Amplicons are formed from mismatched heteroduplexes, preferably by extending the partially digested duplexes after treatment with exonuclease III followed by PCR amplification. The resulting amplicons are inserted into a cloning vector which is used to transform a bacterial host. After host cells are plated and allowed to form colonies, clones are picked and sequenced to identify DNA fragments containing polymorphic sequences.

6 Claims, 4 Drawing Sheets

METHOD OF SCREENING FOR GENETIC POLYMORPHISM

This application is the National Stage of International Application No. PCT/US/99/20047, filed Aug. 31, 1999, which claims the benefit of U.S. Provisional Application No. 60/099,147, filed Sep. 4, 1998.

FIELD OF THE INVENTION

The invention relates generally to methods for identifying polymorphic DNA sequences, and more particularly, to a method of comparing a reference DNA population with a test DNA population for the purpose of identifying sequences that are different.

BACKGROUND

Genetic factors contribute to virtually every disease, conferring susceptibility or resistance, or influencing interaction with environmental factors, Collins et al, Science, 278: 1580–1581 (1997). As genome mapping and sequencing projects advance, more attention is being directed to the problem of sequence variability, both between genomes of the same species and, perhaps more importantly, between genetic regulatory elements and expressed genes of different individuals of the same species. In the area of human health, it is believed that a detailed understanding of the correlation between genotype and disease susceptibility, responsiveness to therapy, likelihood of side-effects, and other complex traits, will lead to improved therapies, to improved application of existing therapies, to better preventative measures, and to better diagnostic procedures. Caskey, Science, 236: 1223–1229 (1987); White and Caskey, Science, 240: 1483–1488 (1988); Lander et al, Science, 265: 2037–2048 (1994); Schafer et al, Nature Biotechnology, 16: 33–39 (1998); and Housman et al, Nature Biotechnology, 16: 492–493 (1998).

Many techniques are available for detecting the presence or absence of a suspected mutation or polymorphic sequence, including direct sequencing, ligation-based assays, restriction fragment length analysis, allele-specific polymerase chain reaction, assays based on differential electrophoretic mobilities, primer extension, mismatch repair enzymes, and specific hybridization, e.g. Taylor, Editor, Laboratory Methods for the Detection of Mutations and Polymorphisms in DNA (CRC Press, Boca Raton, 1997); Cotton, Mutation Detection (Oxford University Press, Oxford, 1997); Landegren et al, Science, 242: 229–237 (1988); Brown, Current Opinion in Genetics and Development. 4: 366–373 (1994): Shumaker et al, Human Mutation, 7: 346–354 (1996); Nikiforov et al, Nucleic Acids Research. 22: 4167–4175 (1994); Pastinen et al, Genome Research, 7: 606–614 (1997); Lisitsyn et al, Science, 259: 946–951 (1993); and the like. However, most of these techniques are not directed to large-scale identification, or surveying, of polymorphic sequences, either for whole genomes or for expressed genes, and several require that the polymorphism be known beforehand. This limitation is significant, as the frequency of polymorphism in unrelated individuals is estimated to average as high as once every several hundred basepairs, e.g. Cooper et al, Human Genetics, 69: 201–205 (1985). Thus, some disease conditions or susceptibilities could depend on the interaction of and/or contributions from large numbers of genetic loci.

It would be highly desirable if there was an approach available that was particularly well suited for large-scale identification of, or surveying, polymorphic or mutated sequences in an individual.

SUMMARY OF THE INVENTION

Accordingly, my invention includes providing methods and materials for carrying out the following objectives: identifying multiple polymorphic sequences in a test DNA population, identifying genes or other sequences in a population carrying novel polymorphisms, identifying differences between two populations of DNA molecules, identifying genes having a polymorphic or mutated sequence, and determining the degree of genetic variation between a test DNA population and a reference DNA population.

My invention achieves these and other objectives by providing methods and materials for identifying member polynucleotides of a test DNA population whose nucleotide sequences differ from those of the corresponding polynucleotides of a reference DNA population. In accordance with the invention, heteroduplexes are formed between polynucleotides of the reference DNA population and those of the test DNA population. Heteroduplexes that contain mismatched base pairs are separated from those that form perfectly matched duplexes, preferably by enzymatically digesting the perfectly matched heteroduplexes and homoduplexes so that only partially double stranded mismatched heteroduplexes remain. The mismatched heteroduplexes are then used to generate amplicons which are sequenced to identify members of the test DNA population whose sequences differ from those of the corresponding members of the reference DNA population. The nature of the sequence difference between the test and reference DNAs is determined by complete sequencing of the test DNA fragment. Materials of the invention include cloning vectors which efficiently accept inserts comprising either reference DNA or test DNA, and kits including the cloning vectors of the invention.

DEFINITIONS

Figure 1A:
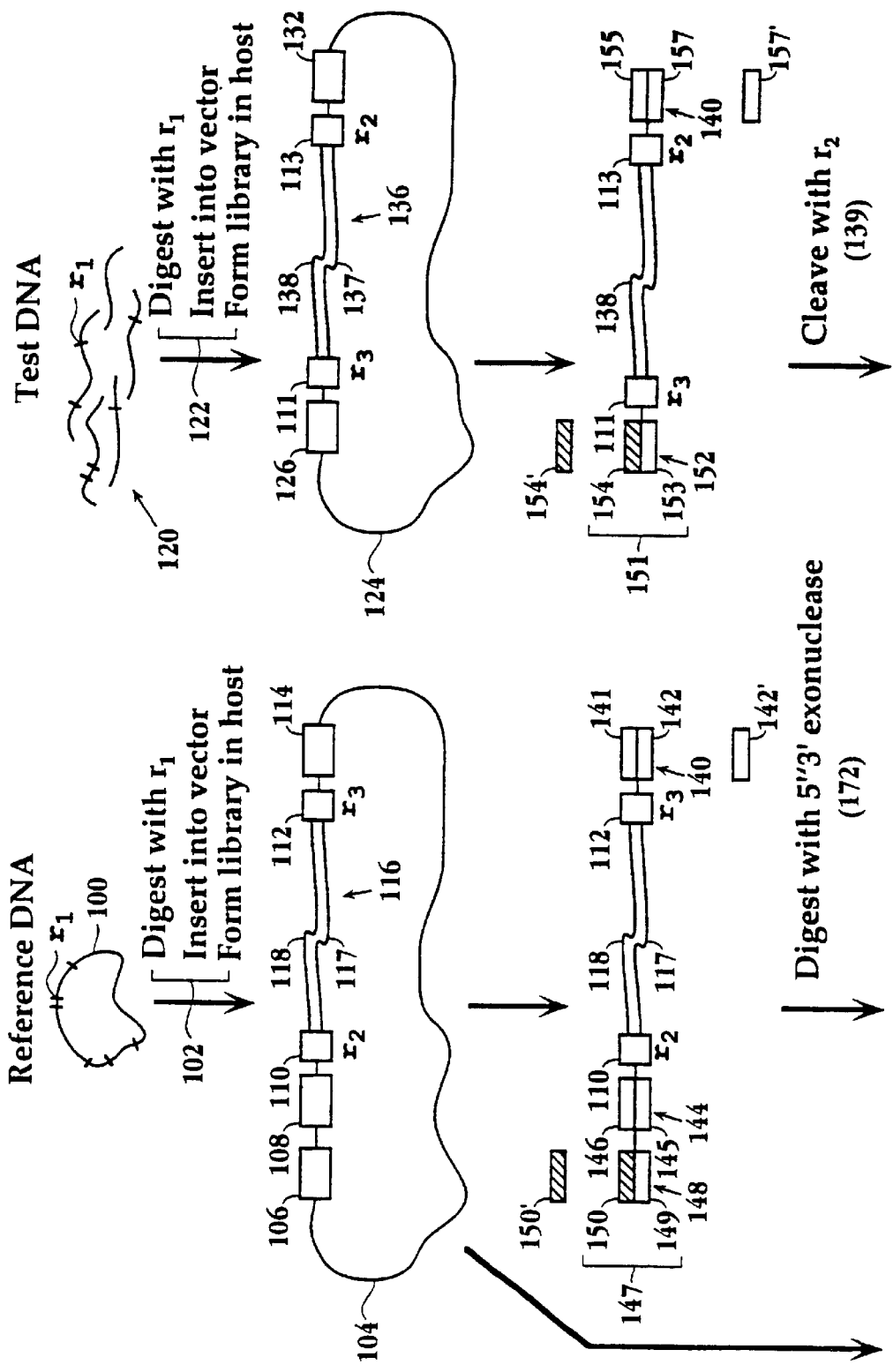
FIGS. 1a–1c illustrates a preferred scheme for carrying out the steps of the invention.

As used herein, the term "complexity" in reference to a population of polynucleotides means the number of different species of polynucleotide present in the population.

As used herein, the term "heteroduplex" means a duplex consisting of two strands of DNA or one strand of DNA and one strand of RNA wherein one strand is derived from a reference DNA molecule and the other strand is derived from a test DNA molecule, e.g. a putative mutant or polymorphic DNA molecule. The two strands of a heteroduplex may form a perfectly matched duplex or they may form a duplex with one or more mismatches and/or one or more insertions or deletions of nucleotides. Usually, heteroduplexes are formed from single stranded DNAs from the same genomic region of two different individuals of the same species.

As used herein, the term "mismatch" means a base pair between any two of the bases A, T (or U for RNA), G, and C other than the Watson-Crick base pairs G-C and A-T. The eight possible mismatches are A-A, T-T, G-G, C-C, T-G, C-A, T-C, and A-G.

As used herein, the terms "mutation" and "polymorphism" are used somewhat interchangeably to mean a DNA molecule, such as a gene, that differs in nucleotide sequence from a reference DNA molecule, or wildtype, by one or more bases, insertions, and/or deletions. The usage of Cotton (cited above) is followed in that a mutation is understood to be any base change whether pathological to an organism or not, whereas a polymorphism is usually understood to be a base change with no direct pathological consequences.

The term "oligonucleotide" as used herein includes linear oligomers of natural or modified monomers or linkages, including deoxyribonucleosides, ribonucleosides, and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units, e.g. 40–60. Whenever an oligonucleotide is represented by a sequence of letters, such as "ATGCCTG." it will be understood that the nucleotides are in 5' 3' order from left to right and that "A" denotes deoxyadenosine. "C" denotes deoxycytidine, "G" denotes deoxyguanosine, "T" denotes thymidine, and "U" denotes uridine, unless otherwise noted. The term "dNTP" is an abreviation for "a deoxyribonucleoside triphosphate," and "dATP", "dCTP", "dGTP", "dTTP", and "dUTP" represent the triphosphate derivatives of the individual deoxyribonucleosides. Usually oligonucleotides comprise the natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce complexity, increase specificity, and the like.

As used herein, "reference population" of DNA, or "reference DNA population," refers to a collection of DNAs, or RNAs derived from it, which is compared to a test population of DNA or RNA, or "test DNA population," by the formation of heteroduplexes between the complementary strands of the reference DNA population and test DNA population. If perfectly matched heteroduplexes form, then the respective members of the reference and test populations are identical; otherwise, they are polymorphic. Typically, the nucleotide sequences of members of the reference population are known and the sequences, and their variants, are listed in sequence databases, such as Genbank. Preferably, a reference population of DNA comprises a cDNA library from a known cell type or tissue source. For example, a reference population of DNA may comprise a cDNA library derived from the tissue of a healthy individual and a test population of DNA may comprise a cDNA library derived from the same tissue of a diseased individual. Reference populations of DNA may also comprise an assembled collection of individual polynucleotides, e.g. genes encoding all of the known p53 variants, or the like, or may comprise genomic DNA.

As used herein, the term "amplicon" refers to a population of identical DNA molecules replicated, or amplified, by a DNA amplification technique, usually polymerase chain reaction (PCR). Thus, a population of amplicons refers to a population of populations of identical DNA molecules, as would be produced if a mixture of DNA molecules were amplified in the same PCR.

As used herein, the term "vector" or "cloning vector" refers to an extrachromosomal genetic element which can be used to replicate a DNA fragment in a host organism. A wide variety of cloning vectors are commercially available for use with the invention, e.g. New England Biolabs (Beverely, Mass.); Stratagene Cloning Systems (La Jolla, Calif.); Clontech Laboratories (Palo Alto, Calif.); and the like. Usually, cloning vectors used with the invention are bacterial plasmids.

DETAILED DESCRIPTION OF THE INVENTION

The present invention is directed to the identification of DNA sequences in a test DNA population that contain polymorphic sequences relative to genes or other DNA sequences in a reference population. An important feature of the invention is the comparison of populations of DNAs rather than individual DNAs one at a time. In accordance with the invention, DNA sequences of the test DNA population that contain sequence differences relative to their counterparts in the reference DNA population are identified by sequencing portions of mismatched heteroduplexes formed by hybridizing member DNA sequences of the respective populations. The sequence information obtained from the mismatched heteroduplexes may then be used to "look up" a corresponding full-length sequence in a nucleotide sequence database, such as Genbank, or the test sequence can be sequenced fully using conventional techniques. As used herein, the term "sequence tag" refers to the nucleotide sequence of such a portion of a DNA sequence. It is possible, of course, that a previously unknown gene or sequence may be identified, but typically a known gene or sequence is identified by conducting a homology search of a database of known gene and/or genomic sequences. Preferably, a sequence tag is long enough to permit the unique identification of the gene or genomic fragment from which the tag is derived. Thus, for smaller genomes, shorter sequence tags may be employed, and for larger genomes, longer sequence tags are required. Preferably, sequence tags are at least nine nucleotides in length: more preferably, sequence tags are at least 15 nucleotides in length. Still more preferably, a sequence tag has a length in the range of 15 to 300 bases.

The reference DNA populations and test DNA populations may be derived from a variety of sources, including genomic DNA, expressed genes, messenger RNA, and the like, of either plant, animal, or microbial origin, and may be from individuals of the same or different species, or from individuals of similar or different geographical or ecological environments. Preferably, the test DNA populations are from one or more individuals having a medical condition, susceptibility, or disease of interest, and the reference DNA populations are from one or more individuals free of such condition, susceptibility, or disease. The test and reference DNA populations are preferably derived from genomic DNA, which allows comparison of expressed as well as non-expressed DNA sequences, such as genetic regulatory elements. Preferably, the reference and test DNA populations are prepared by digesting source DNA, e.g. genomic DNA, with the same restriction endonuclease. The respective fragments are then preferably inserted into cloning vectors to form libraries for storing and manipulating the populations of DNA fragments. Exemplary cloning vectors include pUC19, pNEB193, M13mp, pBluescript II, and the like (New England Biolabs, Beverly, Mass.: Stratagene, La Jolla, Calif.). Preferably, reference and test populations of DNA are prepared by cloning in vectors in order to minimize the random introduction of spurious mutations. If PCR is employed in the preparation, preferably high fidelity DNA polymerases are employed, such as Pfu DNA polymerase, or the like, and/or the number of amplification cycles is minimized.

Another important feature of the invention is the formation of heteroduplexes between single stranded DNA of the test DNA population and substantially complementary single stranded DNA of the reference DNA population. Such single stranded DNA may be produced in a variety of ways, including denaturation by heating, treatment with a chaotropic solvents, and the like, using techniques well known in the art, e.g. Britten et al. Methods in Enzymology, 29: 363–418 (1974): Wetmur et al, J. Mol. Biol., 31: 349–370 (1968). Preferably only complementary single stranded DNA from one population is selected for hybridization with the single stranded DNA of the other population, so that there is no possibility of forming nonproductive homoduplexes. Such stand isolation can be carried out in several ways, including asymmetric PCR, PCR with one nuclease-resistant primer followed by exonuclease digestion, melting the complements from avidin-captured biotinylated strands, and the like, e.g. Birren et al, editors, Genome Analysis: A Laboratory Manual, Vol. 1 (Cold Spring Harbor Laboratory Press, New York, 1997); Hultman et al, Nucleic Acids Research, 17: 4937–4946 (1989); Straus et al, BioTechniques, 10: 376–384 (1991); Nikiforow et al. PCR Methods and Applications, 3: 285–291 (1994); and the like, which references are incorporated by reference. Preferably, single stranded DNA from the respective populations is prepared by PCR with a nuclease-resistant primer followed by exonuclease digestion.

Whenever the method of the invention is applied to populations of DNA that include all or a substantial fraction of complete genomes, particularly mammalian or higher plant genomes, the step of forming heteroduplexes preferably includes a step of forming subpopulations of DNA in order to reduce the complexity of the DNA populations prior to hybridization. As is well known in the art, e.g. Britten et al (cited above), the rate of a hybridization reaction depends on the complexity of the mixture of hybridizing nucleic acid strands. Thus, in order to reduce the time of forming heteroduplexes, the complexities of either one or both the reference DNA and the test DNA populations are preferably reduced prior to carrying out hybridization reactions for forming heteroduplexes. Preferably, complexities are reduced by partitioning the respective populations into subpopulations in well known ways, e.g. differential PCR amplification using sets of primers having different 3'-terminal nucleotides, e.g Pardee et al. U.S. Pat. No. 5,262,311: amplification after ligation of indexing linkers, e.g. Kato, U.S. Pat. No. 5,707,807: Deugau et al, U.S. Pat. No. 5,508,169; and Sibson, U.S. Pat. No. 5,728,524; and the like, which references are incorporated by reference. Preferably, complexities are reduced enough to permit reassociation of ninety percent of the complementary single stranded DNA in 72 hours or less. More preferably, complexity is reduced to permit reassociation of ninety percent of the complementary single stranded DNA in 48 hours or less. Most preferably, complexity is reduced so that reassociation of ninety percent of the complementary single stranded DNA takes place in 16 hours or less.

In embodiments wherein complex genomes, such as human genomes, are compared. Preferably the reference DNA population consists of restriction fragments from an insert of a cloning vector, such as a phage, cosmid, BAC, PAC, YAC, or like system for storing and maintaining large genomic fragments. More preferably, the reference DNA population consists of restriction fragments from a BAC insert. Techniques for construction and manipulation of such cloning vectors is described in Birren et al, editors. Genome Analysis: A Laboratory Manual, Vol. 1, "Analyzing DNA," (Cold Spring Harbor Laboratory Press, New York, 1997); or like references. Preferably, restriction fragments making up a reference DNA population and/or a test DNA population have an average length in the range of several tens of basepairs, e.g. 50, to a few thousand basepairs, e.g. 2000, so that they may be easily cloned in readily available vectors and/or amplified by PCR. More preferably, such restriction fragments have an average length in the range of 50 to 300 basepairs. In further preference, a reference DNA population derived from a BAC insert consists of from several hundred, e.g, two hundred, to several thousand, e.g, two thousand, fragments.

Once heteroduplexes are formed in accordance with the invention, it is important to distinguish heteroduplexes with mismatches from those forming perfectly matched duplexes in a manner which permits isolation of a portion of each of the mismatched heteroduplexes. This may be accomplished with application of so-called chemical mismatch recognition techniques as well as enzymatically based mismatch recognition techniques, such as disclosed widely in the mutation detection literature, e.g. Taylor (cited above), Cotton (cited above); Cotton, U.S. Pat. No. 5,698,400; Modrich et al, U.S. Pat. No. 5,702,894; Ganguly et al, Genomics, 4: 530–538 (1989); Ganguly et al, Nucleic Acids Research, 18: 3933–3939 (1990); Lu et al, Genomics, 14:249–255 (1992); Ellis et al, Nucleic Acids Research, 22: 2710–2711 (1994); Maniatis et al, U.S. Pat. No. 4,946,773; Smooker et al. Mutation Research, 288: 65–77 (1993): and the like, which references are incorporated by reference.

Preferably, mismatched heteroduplexes are distinguished from perfectly matched heteroduplexes and homoduplexes by enzymes that recognize, or are affected by, mismatched sequences. More preferably, such enzymes include resolvases. RNase As, methyl-directed mismatch repair enzymes, mutY proteins, cel I, exonucleases, and the like.

Most preferably, mismatched heteroduplexes are recognized by a single stranded exonuclease which requires a double stranded DNA substrate. That is, the exonuclease binds to a double stranded DNA substrate, but digests only one of the two strands of the substrate. When such an exonuclease encounters a mismatched duplex, which disrupts the substrate structure, digestion is significantly inhibited, or stops altogether. An example of such an exonuclease is exonuclease III from *Escherichia coli,* which is described fully in Rogers et al. Methods in Enzymology, 65: 201–211 (1980); and Guo et al, Methods in Enzymology, 100: 60–97 (1983) (which references are incorporated by reference). Exonuclease III is a standard reagent of molecular biology and is widely available commercially, e.g. New England Biolabs (Beverly, Mass.).

Figure 1B:
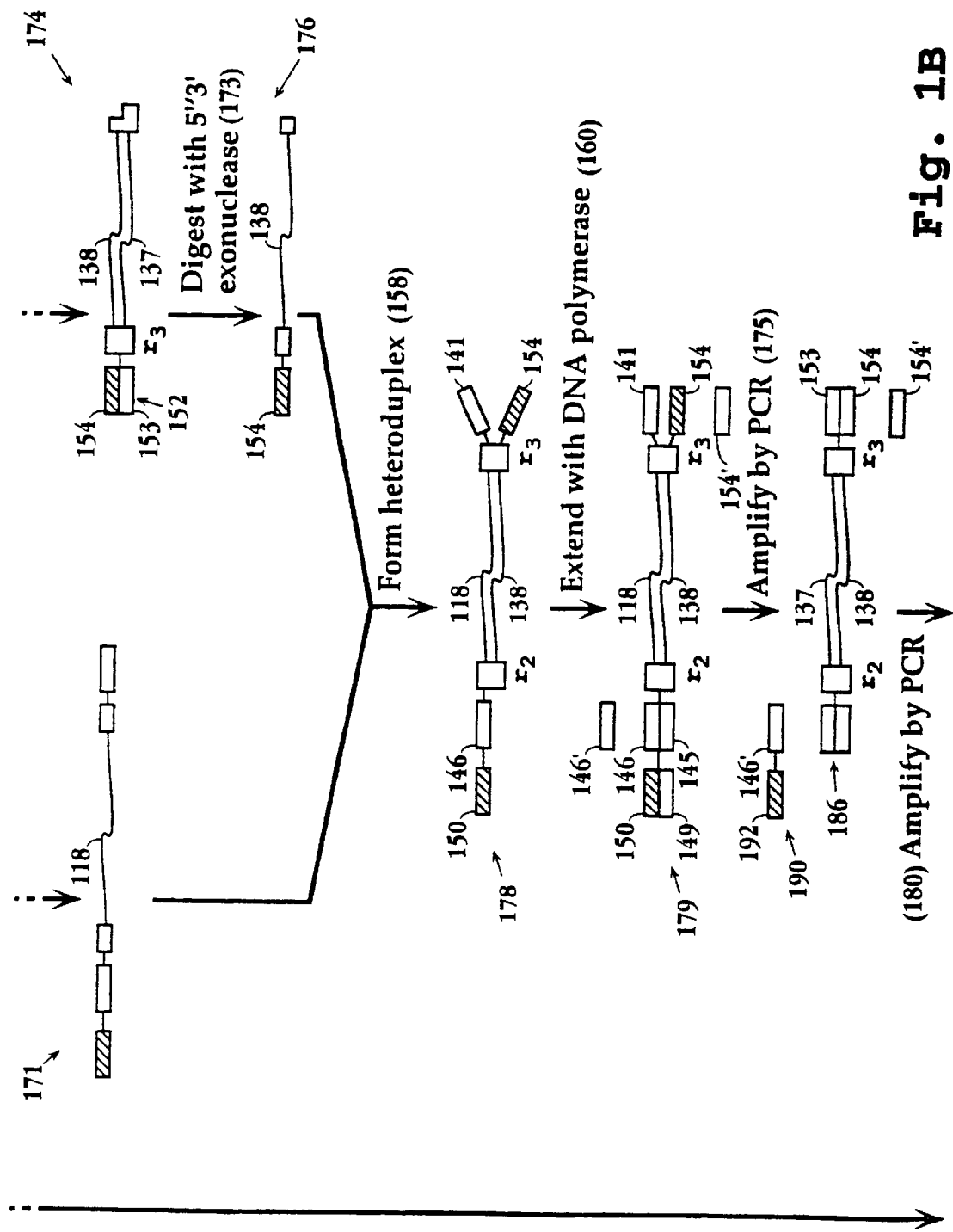
Figure 1C:
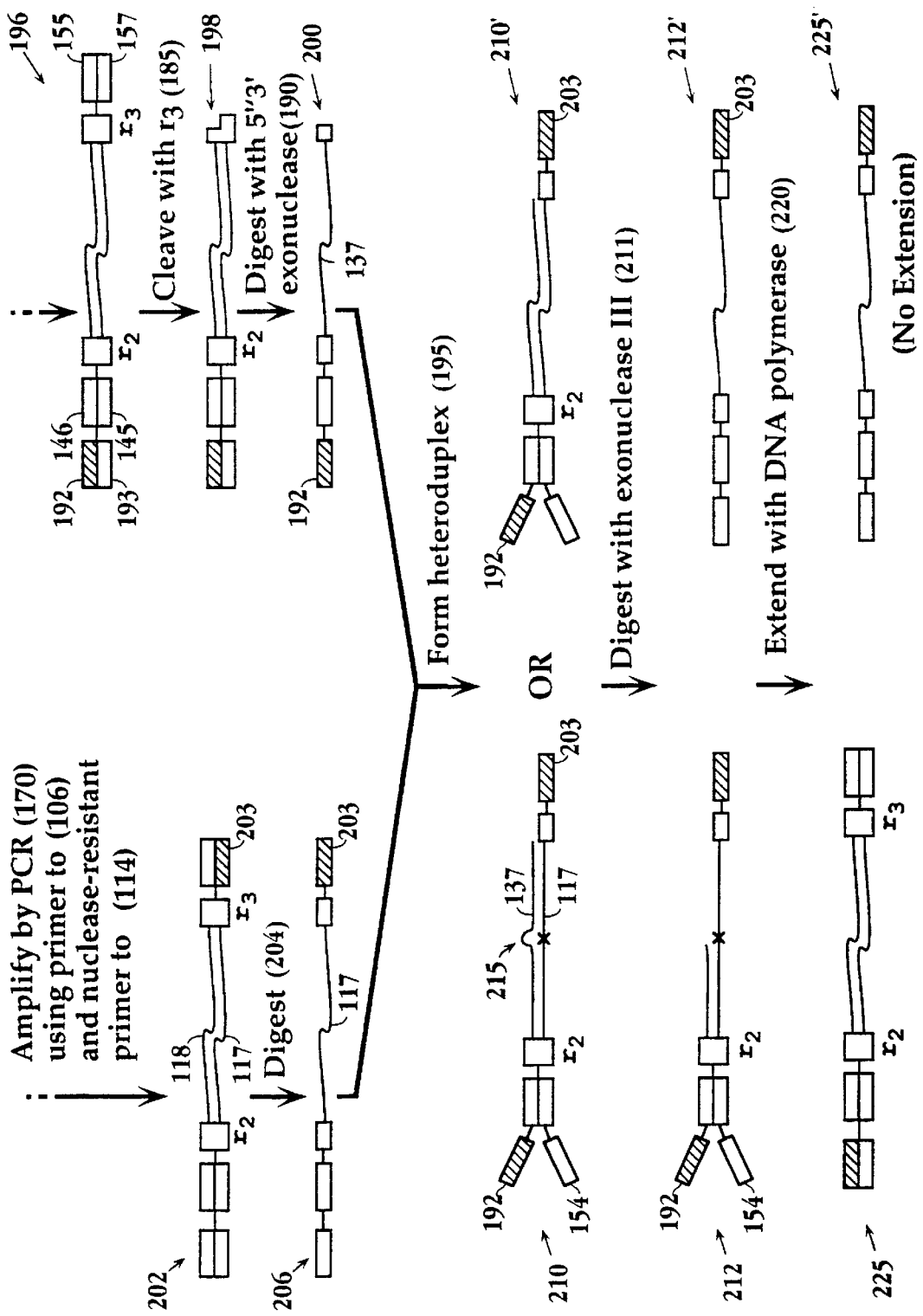

A preferred embodiment of the invention employing exonuclease III is shown schematically in FIGS. 1*a* through 1*c*. As shown in FIG. 1*a*, a reference DNA population is formed by steps (102) of digesting BAC (100) with restriction endonuclease $r_1$, inserting the resulting fragments into cloning vector (104), using conventional protocols, e.g. Ausubel et al, editors. Current Protocols in Molecular Biology (John Wiley & Sons, New York, 1997), and transforming a suitable host to form a recombinant library. Cloning vector (104) is constructed with the following elements adjacent to a restriction endonuclease recognition site for accepting the fragments of the reference DNA population:

first primer binding site (106), second primer binding site (108), restriction endonuclease recognition site $r_2$ (110), restriction endonuclease recognition site $r_3$ (112), and third primer binding site (114). The first, second, and third primer binding sites have different sequences so that a primer directed to one does not cross hybridize or anneal to any other. Reference DNA fragment (116) with strands (117) and (118) is shown in the vector. After insertion of the reference DNA fragments into vector (104), a suitable host is transformed and a recombinant library is created.

A test DNA population is formed by steps (122) of digesting a sample of test DNA (120) with restriction endonuclease $r_1$, inserting the resulting fragments into cloning vector (124) using conventional protocols, and forming a recombinant library. The selection of cloning vectors (104) and (124) is not critical to the invention. Commercially available vectors, such as pUC19, pBS+/− (Strategene Cloning Systems, La Jolla, Calif.), and the like, are suitable for use with the invention with straight forward modifications to generate the preferred elements. Selection of restriction endonucleases $r_1$, $r_2$, and $r_3$, are likewise not critical to the invention and a significant degree of latitude may be exercised in their selection. Preferably, $r_1$, $r_2$, and $r_3$ have different recognition sites. Cloning vector (124) is constructed with the following elements adjacent to a restriction endonuclease recognition site for accepting the fragments of the test DNA population: fourth primer binding site (126), restriction endonuclease recognition site $r_3$ (111), restriction endonuclease recognition site $r_2$ (113), and fifth primer binding site (132). The sequences of third primer binding site (114) and fifth primer binding site (132) are the same, but the sequence of fourth primer binding site (126) is different from that of any of the other primer binding sites so that a primer hybridizing or annealing to it would not cross hybridize to any of the others. Test DNA fragment (136) with strands (137) and (138) is shown in the vector. After insertion of the test DNA fragments into vector (124), a suitable host is transformed and a recombinant library is created.

After formation of libraries of reference fragments in vector (104) and test fragments in vector (124), a series of steps (158, 160, 175) are preferably implemented to select only those fragments from the test fragment library that correspond to fragments from the reference DNA population. Such selection may be carried out as follows: First, amplicon (147) is formed by carrying out a PCR using vector (104) as a target DNA and primers (150') and (142') which are specific for strands (149) and (141), respectively. PCR products are purified after amplification by use of commercially available solid phase column purification systems, e.g. QIAquick PCR Purification kit (Qiagen GmbH, Hilden, Germany). Primer (150') is cross-hatched to indicate that it contains exonuclease resistant linkages. As a result, the 5' end of strand (150) of amplicon (147) is resistant to 5'→3' exonuclease digestion. Many different nuclease-resistant moieties may be employed where called for in the invention provided that such moieties are compatible with PCR conditions. For example, Eckstein, editor, Oligonucleotides and Analogues: A Practical Approach (IRL Press, Oxford, 1991); Froehler, U.S. Pat. No. 5,256,775; Mesmaeker et al, Current Opinion in Structural Biology, 5: 343–355 (1995). Crooke et al, Exp. Opin. Ther. Patents, 6: 855–870 (1996); and like references, describe several nuclease-resistant oligonucleotides. Preferably, phosphorothioate linkages between nucleosides are used to confer nuclease resistance. Amplicon (147) is digested (172) with a 5'→3' exonuclease, e.g. T7 gene 6 exonuclease (available from United States Biochemical), to give single stranded DNA (171), following the protocol of Straus et al, BioTechniques 10: 376–384 (1991). Separately, amplicon (151) is formed by carrying out a PCR using vector (124) as a target DNA and nuclease-resistant primer (154') and standard primer (157') which are specific for strands (153) and (155), respectively. The 5' end of strand (154) of amplicon (151) is resistant to 5'→3' exonuclease digestion. Amplicon (151) is cleaved (139) with endonuclease $r_2$ to remove fifth primer binding site (132), after which resulting fragment (174) is digested (173) with a 5'→3' exonuclease to give single stranded DNA (176). Single stranded DNAs (171) and (176) are then combined to form (158) heteroduplexes (178) with non-complementary ends (141) and (154). Simple strand (138) is extended (160) with a DNA polymerase to form heteroduplex (179), after which heteroduplex (179) is amplified (175) in a PCR using primers (146') and (154') complementary to regions (145) and (153), respectively (the latter region (153) being created after the first extension of primer (146')). Thus, segment (141) is not replicated in the PCR and single strand (118) is replaced by complement (137) of strand (138) so that each amplicon (186) contains a replicate of a test DNA fragment.

Amplicon (186) is further amplified (180) in a PCR using primers (190) and (154') so that amplicon (196) is formed. Primer (190) comprises a 3' portion (146') complementary to segment (145) and a 5' portion (192) which contains nuclease resistant linkages and which extends beyond the end of amplicon (186) so that, after amplification, amplicon (196) contains a nuclease-resistant 5' end (192). After cleavage with restriction endonuclease $r_3$ (185) to produce duplex (198), duplex (198) is digested (190) with a 5'→3' exonuclease to produce single stranded DNA (200).

Separately from the above, amplicon (202) is produced in a PCR using vector (104) as a target DNA and primers annealing to regions (148) and (141). The primer annealing to region (141) is resistant to digestion by 5'→3' exonucleases, so that amplicon (202) contains nuclease-resistant region (203). After digestion (204) of amplicon (202) with a 5'→3' exonuclease to produce single stranded DNA (206), single stranded DNA (206) is combined with single stranded DNA (200) to form either heteroduplex (210) when mismatches (215) are present between the test DNA strand and the corresponding reference DNA strand or heteroduplex (210') when the test DNA and reference DNA strands are perfectly complementary. The heteroduplexes (210) and (210') are treated (211) with exonuclease III, or like exonuclease, to digest the 3' recessed strands of the heteroduplexes. At sites on heteroduplexes (212) where the double stranded structure is disrupted, such as by mismatch (215), digestion is halted and partially double stranded structure (212) is formed. In contrast, perfectly matched heteroduplexes (210') are converted into single stranded form (212'). Partially double stranded structures (212) are rendered fully double stranded by treatment (220) with a DNA polymerase having 3'→5' exonuclease activity. Such a polymerase extends strand (137), cleaves the overhanging 3' end (149), then extends the same strand using region (192) as a template to form completed a duplex (225). Duplex (225) contains a fragment of the reference DNA population.

After amplification, duplex (225) is inserted into a conventional cloning vector, e.g. via restriction sites $r_2$ and $r_3$, and a suitable bacterial host is transformed and plated. Clones are picked from colonies and inserts of such clones are sequenced to identify fragments of the reference DNA population whose counterparts in the test DNA population contain polymorphic sequences. The polymorphism of the test DNA fragment is identified by cloning and sequencing the test DNA fragment using conventional techniques. For example, in the above embodiment, primers may be constructed based on the knowledge of the reference DNA sequence for amplifying the counterpart fragment from the test DNA population.

As mentioned above, the invention includes kits for carrying out the method of detecting polymorphisms. Such kits comprise cloning vectors for producing reference DNA populations and test DNA populations, primers for generating amplicons of the method, and a 3'→5' exonuclease for generating partially double stranded duplexes from amplicons having mismatched sequences. More preferably, kits further comprise 5'→3' exonuclease-resistant primers for generating single stranded DNA from double stranded amplicons and a 5'→3' exonuclease for carrying out such reactions. Still more preferably, such kits further include instructions for carrying out the steps of the method of the invention, and cloning vectors having the structures described in FIGS. 1a–c for producing reference DNA populations and test DNA populations. Such kits may also include restriction endonucleases $r_1$, $r_2$, and $r_3$, as well as the appropriate reaction buffers for their use and the use of other enzymes, such as DNA polymerases, in the method of the invention.

System for Efficient Cloning of Genomic Fragments

Figure 2:
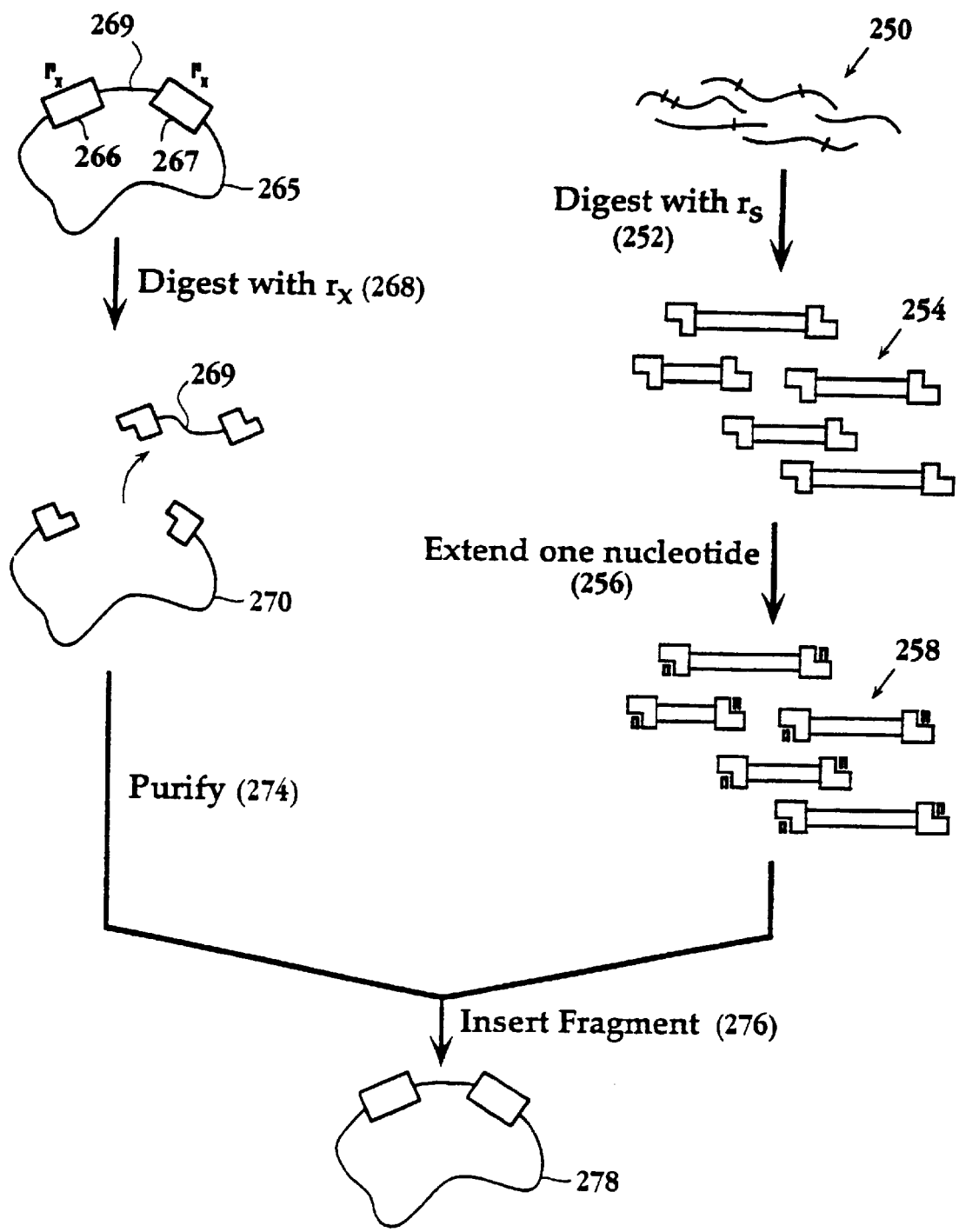
FIG. 2 schematically illustrates a preferred cloning system for constructing reference DNA populations and test DNA populations in accordance with the invention.

Preferably, DNA fragments of test and reference DNA populations are cloned with the system shown schematically in FIG. 2. A key feature of the cloning system is the production of fragments that can neither form concatemers nor self ligate. That is, after digestion (252) of the test or reference DNA (250) with a restriction endonuclease $r_S$ that produces 3' recessed ends, the ends are treated (256) to render the protruding strands non-self complementary. Preferably, this is accomplished by extending (256) the 3' recessed strand by one nucleotide by a conventional DNA polymerase reaction in the presence of a single dNTP to produce modified restriction fragments (258). For example, if the test or reference DNA is cleaved with restriction endonuclease Bcl I, fragments with the following ends are produced:

| 5' ...NT | GATCAN ... 3' |
|---|---|
| 3' ...NACTAC | TN ... 5' |

The recessed 3' ends of the fragments are extended with a polymerase in the presence of dGTP to produce the following ends:

| 5' ...NTC | GATCAN ... 3' |
|---|---|
| 3' ...NACTAC | GTN ... 5' |

Since these ends are not complementary, the fragments will not be joined to one another in a standard ligation reaction used to insert the fragment into a vector. Preferably, $r_S$ is any type II restriction endonuclease that has an uninterrupted palindromic recognition site and that leaves a 3' recessed strand upon cleavage. More preferably, a palindromic four-nucleotide 5' protruding strand (as shown above) is produced upon cleavage with $r_S$.

Cloning vector (265) is designed to have a cloning site flanked by two restriction endonuclease recognition sites (266) and (267) for restriction endonuclease $r_X$. Preferably, the cloning site of vector (265) contains "stuffer" fragment (269) which is removed (268) prior to insertion of fragments (258) into "opened" vector (270). $r_X$ is selected to produce ends compatible with the modified ends of fragments (258), which generally must be one nucleotide shorter that the overhangs produced by $r_S$. A stuffer fragment permits an opened vector (i.e. cleaved at 266 and 267) to be conveniently isolated by gel electrophoresis, or like technique that differentiates DNA fragments by size. Preferably, the stuffer fragment is large enough to permit efficient and convenient isolation of an opened vector. More preferably, a stuffer fragment (269) is between ten and several hundred, e.g. 200, basepairs in length. $r_X$ must produce a 5' protruding strand with a nucleotide sequence complementary to the protruding strands of modified fragments (258). Since the extension step (256) destroys the palindromic character of the ends of fragments (258), $r_X$ must be selected from restriction endonucleases that allow the production of ends in vector (265) that are complementary to such non-palindromic ends. Accordingly, $r_X$ is selected from enzymes that can cleave within arbitrary or substantially arbitrary sequences of nucleotides, which typically include either type IIs restriction endonucleases or type II restriction endonucleases having interrupted palindromic recognition sites. Preferably, sites (266) and (267) are for the same enzyme. More preferably, sites (266) and (267) are for the same type IIs restriction endonuclease. Preferably, whenever (266) and (267) are for type IIs endonucleases, the recognition sites are internal to stuffer fragment (269) such that the cleavage sites of the enzymes form the boundary of the stuffer fragment in the vector. Exemplary combinations of restriction endonucleases for use with the invention are listed in the following table:

| Exemplary $r_x$ | Recognition Sequence | Exemplary $r_s$ | Recognition Sequence |
|---|---|---|---|
| Sap I | gctcttc (1/4) | Any type II producing 4-base 5' protruding strand. | |
| Ear I | ctcttc (1/4) | | |
| Ksp632 I | ctcttc (1/4) | | |
| Mwo I | gcnn/nnnnngc | Any type II producing 4-base 5' protruding strand. | |
| Blp I | gc/tnagc | Afl II | c/ttaag |
| Bsu36 I | cc/tnagg | | |
| Dde I | c/tnag | | |
| Hinf I | g/antc | Tsp509 I | /aatt |
| | | Eco RI | g/aattc |
| EcoO109 I | rg/gnccy | Eag I | c/ggccg |
| Sau96 I | g/gncc | | |

Preferably, $r_X$ is Sap I and $r_S$ is selected from the set of "gate" restriction endonucleases, which provides some convenience in selecting compatible cloning vectors. This set of restriction endonucleases includes Sau 3A I, Dpn II, Mbo I, Bgl II, Bam HI, Bcl I, Bst YI, and the like.

Preferably, vector (265) is constructed from a pUC19 by inserting two Sap I recognition sites in its polylinker region. Prior to such insertion, the sole Sap I site in pUC19 is removed by digesting a pUC19 with Tfi I, followed by isolation and recircularization of the large fragment to produce pUC19'. The following fragment (upper strand: SEQ ID NO:1; lower strand: SEQ ID NO:2) is inserted into pUC19' after digestion with Bam HI and Hind III:

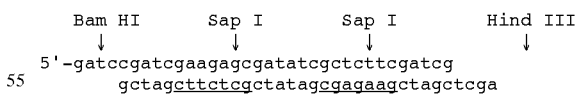

The resulting vector accepts modified fragments (258) derived from DNA digested with a restriction endonuclease from the set of "gate" restriction endonucleases.

Additional elements may be added to cloning vector (265) by straight forward manipulations. For example, an embodiment of cloning vector (104) is readily constructed by inserting the following fragment (upper strand: SEQ ID NO:3, lower strand: SEQ ID NO:4) which adds a Bgl II site into the Eco RI/Bam HI-digested pUC19':

```
    Eco RI Bgl II    Sap I             Sap I        Bam HI
       ↓    ↓          ↓                 ↓             ↓
5'-aattcagatctgatcgaagagcgatatcgctcttcgatcgtcg
       gtctagactagcttctcgctatagcgagaagctagcagcctag
```

Vector sequences may be used for primer binding sites site. (106), (108), and (114).

The corresponding embodiment of cloning vector (124) may be constructed by inserting the following fragment (upper strand: SEQ ID NO:5: lower strand: SEQ ID NO:6) into an Eco RI/Hind III-digested pUC19':

```
    Eco RI              Bam HI   Sap I          Sap I      Bgl II  Hind III
       ↓                  ↓        ↓              ↓           ↓       ↓
5'-aattctttaaaaccttcctggatccgatcgaagagcgatatcgctcttcgatcagatcta
       gaaattttggaaggacctaggctagcttctcgctatagcgagaagctagtctagattcga
                         ↑
       primer binding site(126)
``` where primer binding site (126, double underlined sequence) is added along with a Bam HI site and a Bgl II

---

What is claimed is:

1. A method of identifying polymorphic DNA sequences in a test DNA population, the method comprising the steps of:

(a) providing a reference DNA population;

(b) forming a population of heteroduplexes from single stranded DNA of the reference DNA population and single stranded DNA of the test DNA population, said heteroduplexes having at one terminus a region in which both strands are in single stranded form;

(c) treating said heteroduplexes with an exonuclease whose substrate is duplex DNA, such that said exonuclease converts substantially every perfectly matched duplex to single stranded DNA and substantially every mismatched duplex to partially double stranded DNA;

(d) extending said partially double stranded DNA to form double stranded heteroduplexes;

(e) amplifying the double stranded heteroduplexes to form a population of amplicons; and (f) determining the nucleotide sequence of a portion of each amplicon so that polymorphic DNA sequences of the test DNA population are identified.

2. The method of claim 1, wherein members of said reference DNA population are provided in a first cloning vector, and members of said test DNA population are provided in a second cloning vector, wherein the first cloning vector has a first primer binding site, a second primer binding site, a third primer binding site, and a cloning site disposed between the second and third primer binding sites, and the second cloning vector has a fourth primer binding site, a fifth primer binding site, and a cloning site disposed between the fourth primer binding site and the fifth primer binding site, wherein the fifth primer binding site has a nucleotide sequence identical to said third primer binding site, and the sequence of the fourth primer binding site is different from that of any of the other primer binding sites.

3. The method of claim 2, wherein said single stranded DNA of said reference DNA population is generated by amplifying said members of said reference DNA population in a polymerase chain reaction, using a nuclease-resistant primer specific for said first primer binding site and a primer specific for said third primer binding site, to form an amplicon having a single strand with a nuclease-resistant 5' end, and digesting the amplicon with a 5'→3' exonuclease.

4. The method of claim 3 wherein said single stranded DNA of said test DNA population is generated by amplifying said members of said test DNA population in a polymerase chain reaction using a nuclease-resistant primer specific for said fourth primer binding site and a primer specific for said fifth primer binding site to form an amplicon having a single strand with a nuclease-resistant 5' end, and digesting the amplicon with a 5'→3' exonuclease.

5. The method of claim 1 wherein said step of forming a population of heteroduplexes includes partitioning said test DNA population into subpopulations and separately forming subpopulations of heteroduplexes from single stranded DNA of said reference DNA population and single stranded DNA from each subpopulation of said test DNA population.

6. The method of claim 5 wherein said subpopulations of said test DNA population and said reference DNA population have complexities which permit at least ninety percent of heteroduplexes of said subpopulations of heteroduplexes to be formed in seventy-two hours or less.

* * * * *

SEQUENCE LISTING

<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: polylinker

<400> SEQUENCE: 1
gatccgatcg aagagcgata tcgctcttcg atcg                           34

<210> SEQ ID NO 2
<211> LENGTH: 34
<212> TYPE: DNA
<213> ORGANISM: Artificial Sequence
<220> FEATURE:
<223> OTHER INFORMATION: polylinker, complementary to SEQ 1

<400> SEQUENCE: 2
agctcgatcg aagagcgata tcgctcttcg atcg                           34

<210> SEQ ID NO 3
<211> LENGTH: 43
<212> TYPE: DNA
<213> ORGANISM: Artificial Sequence
<220> FEATURE:
<223> OTHER INFORMATION: polylinker

<400> SEQUENCE: 3
aattcagatc tgatcgaaga gcgatatcgc tcttcgatcg tcg                 43

<210> SEQ ID NO 4
<211> LENGTH: 43
<212> TYPE: DNA
<213> ORGANISM: Artificial Sequence
<220> FEATURE:
<223> OTHER INFORMATION: polylinker, complementary to SEQ 3

<400> SEQUENCE: 4

-continued

```
gatccgacga tcgaagagcg atatcgctct tcgatcagat ctg        43

<210> SEQ ID NO 5
<211> LENGTH: 60
<212> TYPE: DNA
<213> ORGANISM: Artificial Sequence
<220> FEATURE:
<223> OTHER INFORMATION: polylinker

<400> SEQUENCE: 5
aattctttaa aaccttcctg gatccgatcg aagagcgata tcgctcttcg atcagatcta        60

<210> SEQ ID NO 6
<211> LENGTH: 60
<212> TYPE: DNA
<213> ORGANISM: Artificial Sequence
<220> FEATURE:
<223> OTHER INFORMATION: polylinker, complementary to SEQ 5

<400> SEQUENCE: 6
agcttagatc tgatcgaaga gcgatatcgc tcttcgatcg gatccaggaa ggtttaaag        60
```